US00PP28993P2

(12) United States Plant Patent
Radler

(10) Patent No.: US PP28,993 P2
(45) Date of Patent: Feb. 27, 2018

(54) FLORIBUNDA ROSE PLANT NAMED 'RADSHINING'

(50) Latin Name: *Rosa hybrida*
Varietal Denomination: Radshining

(71) Applicant: The Conard-Pyle Company, West Grove, PA (US)

(72) Inventor: William J. Radler, Greenfield, WI (US)

(73) Assignee: THE CONRAD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/330,642

(22) Filed: Oct. 24, 2016

(51) Int. Cl.
*A01H 5/02* (2006.01)

(52) U.S. Cl.
USPC ..... Plt./149

(58) Field of Classification Search
USPC ..... Plt./149
See application file for complete search history.

*Primary Examiner* — Annette H Para
(74) *Attorney, Agent, or Firm* — Buchanan Ingersoll & Rooney PC

(57) ABSTRACT

A new and distinct variety of Floribunda rose plant herein referred to by its cultivar name, 'Radshining', is provided which forms in abundance on a substantially continuous basis attractive, cup-shaped, deep pink colored blossoms. The vegetation is vigorous and the growth habit is very bushy and upright. Attractive, glossy, dark green foliage is formed. Very good disease resistance is exhibited, particularly with respect to black spot, rust, and mildews. Additionally, the new variety is particularly well suited for growing as distinctive ornamentation in the landscape.

1 Drawing Sheet

Botanical/commercial classification: *Rosa hybrida*/Floribunda Rose Plant.

Varietal denomination: cv. Radshining.

SUMMARY OF THE INVENTION

The new variety of *Rosa hybrida* Floribunda rose plant of the present invention was created during June 2003 at Greenfield, Wis., U.S.A., by artificial pollination wherein two parents were crossed which previously had been studied in the hope that they would contribute the desired characteristics. The female parent (i.e., the seed parent) was the 'WEKbipuhit' variety (U.S. Plant Pat. No. 11,513). The male parent (i.e., the pollen parent) of the new variety was the 'Radmis' variety (non-patented in the United States). The parentage of the new variety can be summarized as follows:

'Wekbipuhit'×'Radmis'.

The seeds resulting from the above pollination were sown and small plants were obtained which were physically and biologically different from each other. Selective study resulted in the identification of a single plant of the new variety.

It was found that the new Floribunda rose plant of the present invention possesses the following combination of characteristics:

(a) abundantly and substantially continuously forms attractive, cup-shaped, deep pink colored blossoms,
(b) exhibits a very bushy and upright growth habit,
(c) forms vigorous and strong vegetation,
(d) forms attractive ornamental glossy, dark green foliage,
(e) exhibits very good disease resistance, particularly with respect to black spot, rust, and mildews, and
(f) is well suited for providing attractive ornamentation.

A new rose variety is provided displaying attractive, cup-shaped deep pink blossoms combined with substantially continuous blossoming and very good disease resistance.

The new variety well meets the needs of the horticultural industry. It can be grown to advantage as ornamentation in parks, gardens, public areas, and in residential landscapes. Accordingly, the plant is particularly well suited for growing in the landscape.

The new variety can be readily distinguished from its ancestors upon an inspection of the blossoms. More specifically, the new variety can be readily distinguished from the seed parental variety, 'WEKbipuhit' (U.S. Plant Pat. No. 11,513), in that the new variety displays sixteen petals on average and the seed parent 'WEKbipuhit' displays more petals, 24-28 on average. The new variety also differs from the seed parent in the color of the blooms in that 'Radshining' displays deep pink blooms whereas 'WEKbipuhit' displays mauve colored blooms. The new variety can be readily distinguished from the pollen parent, 'Radmis' (non-patented in the United States), in that the new variety exhibits deep pink colored blooms whereas the pollen parent displays peach blooms with tones of yellow and pink in coloration.

The new variety can be readily distinguished from other Floribunda roses such as 'Radprov' (U.S. Plant Pat. No. 23,582) in that the new variety exhibits blooms with 16 petals on average and 'Radprov' displays blooms with 80-90 petals on average.

The characteristics of the new variety have been found at Wasco, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radshining', and will be marketed under the SHINING MOMENT Trademark.

BRIEF DESCRIPTION OF THE PHOTOGRAPHS

The accompanying photograph shows, as nearly true as it is reasonably possible to make the same in a color illustration of this character, typical blossoms of the new variety. The rose plant of the new variety illustrated herein was approximately three years of age and was grown outdoors on its own roots in West Grove, Pa., U.S.A. when it was observed in June 2015.

FIG. 1 shows close view of the blossoms and foliage of the new variety.

DETAILED BOTANICAL DESCRIPTION

The chart used in the identification of colors is that of The Royal Horticultural Society (R.H.S. Colour Chart—1995 Edition), London, England. The description is based on the observation of two-year-old specimens of the new variety during June while growing in ground on their own roots at West Grove, Pa., U.S.A.

Class: Floribunda Rose.

*Variety*.—'Radshining'.

Plant:

*Height*.—Commonly up to approximately 1.4 m on average of growth.

*Width*.—Commonly approach approximately 90 cm on average.

*Habit*.—Very bushy and upright.

Stems:

*Length*.—Main stems commonly approximately 60 cm on average, and secondary stems commonly approximately 13 cm on average.

*Color*.—Near Yellow-Green Group 144B on young stems, and commonly near Yellow-Green Group 144A on old wood.

*Thorns*.—Size: commonly approximately 5 mm in length on average and approximately 4 mm in width on average at the point of attachment when young, and approximately 1 cm in length on average and approximately 4 mm in width on average at the point of attachment when old. Color: commonly near Greyed-Purple Group 183A on young stems, and near Red-Purple Group 59A when old.

Leaves:

*Size*.—Commonly approximately 11 cm in length on average, and approximately 9 cm in width on average for a five-leaflet leaf.

*Leaflets*.—Number 3, 5, and 7. Length: approximately 5 cm on average for a terminal leaflet, and approximately 4 cm on average for a lower leaflet. Width: approximately 3.5 cm on average for a terminal leaflet, and approximately 2.5 cm on average for a lower leaflet. Shape: generally ovate. Margins: serrate. Texture: generally smooth on the upper and under surfaces. Color: (when young): Upper surface: near Greyed-Purple Group 183A. Under surface: near Greyed-Purple Group 183A. Color (when fully mature): Upper surface: near Green Group 137A. Under surface: near Green Group 147B.

Inflorescence:

*Number of flowers*.—Commonly singly or in a cluster of approximately 1 to 4 blossoms on average per stem, and commonly with approximately 15 blossoms on average being present on the plant at a given time.

*Peduncle*.—Near Yellow-Green Group 144A overlaid with Red-Purple Group 59A in coloration, commonly approximately 3.5 cm in length on average, approximately 3 mm in diameter on average, and commonly moderately covered with small flexible thorns less than 2 mm in length.

*Sepals*.—Upper surface: covered with short pubescence, and commonly near Green Group 138B in coloration. Under surface: commonly puberulent, and commonly near Yellow-Green Group 144A in coloration. Size: commonly approximately 3.5 cm in length on average, and approximately 8 mm in width at the base. Margin: entire, and commonly with an extension on three of the sepals measuring approximately 8 mm in length on average and approximately 2 mm in width on average. Number: five.

*Buds*.—Shape: generally ovoid. Length: approximately 2.5 cm on average. Diameter: approximately 1.5 cm on average. Color: when opening, near Red-Purple Group 63A.

*Flower*.—Form: semi-double, cuplike. Diameter: commonly approximately 10 cm on average when fully open. Color (when opening begins): Upper surface: near Yellow Group 2A at the point of attachment transitioning to near Red-Purple Group 60C moving toward the apex and then to near Red-Purple Group 60D. Under surface: near Yellow Group 2A at the point of attachment transitioning to near Yellow-Orange Group 20B moving toward the apex and then to near Red-Purple Group 61C. Color (at end of blooming): Upper surface: near Yellow-White Group 158A at the point of attachment transitioning to near Red-Purple Group 70B towards the apex. Under surface: near Yellow-White Group 158C at the point of attachment transitioning to near Red-Purple Group 70C towards the apex. Fragrance: slight. Petal number: commonly approximately 16 on average under normal growing conditions. Petal length: commonly approximately 4.5 cm on average. Petal width: commonly approximately 5 cm on average. Petal shape: broadly obovate. Petal margin: entire. Petal apex shape: obtuse with a slightly wavy margin. Petal base shape: rounded. Margin: entire. Petal drop: good, the petals commonly detach cleanly and freely drop upon full maturity. Stamen number: approximately 100 on average. Anthers: number approximately 100 on average and commonly near Yellow-Orange Group 17B in coloration. Filaments: approximately 7 mm in length, and the coloration is near Yellow Group 13A. Pollen: commonly present in a moderate quantity, and near Yellow-Orange Group 21A in coloration. Pistils: separate and free, and commonly number approximately 40 on average. Styles: commonly approximately 3 mm in length and near Orange Group 27A. Stigma: commonly approximately 1 mm in diameter on average, and near Yellow-Orange Group 18A in coloration. Receptacle: commonly substantially round in shape, approximately 1 cm in diameter, smooth in texture, near Yellow-Green Group 144A in coloration, and with achenes commonly being present on the bottom and wall.

Development:

*Vegetation*.—Dark green, vigorous, and strong.

*Blossoming*.—Abundant and substantially continuous from spring to frost.

*Resistance to diseases*.—Very good resistance, particularly with respect to black spot, rust, and mildews.

Plants of the 'Radshining' variety have not been observed under all possible environmental conditions to date. Accordingly, it is possible that the phenotypic expression may vary somewhat with changes in light intensity and duration, cultural practices, and other environmental conditions.

I claim:

1. A new and distinct rose plant characterized by the following combination of characteristics:

(a) abundantly and substantially continuously forms attractive cup-shaped, deep pink blossoms, (b) exhibits very bushy and upright growth habit, (c) forms vigorous and strong vegetation, (d) forms attractive ornamental glossy, dark green foliage, (e) exhibits very good disease resistance particularly with respect to black spot, rust and mildews, and (f) is well suited for providing attractive ornamentation; substantially as herein shown and described.

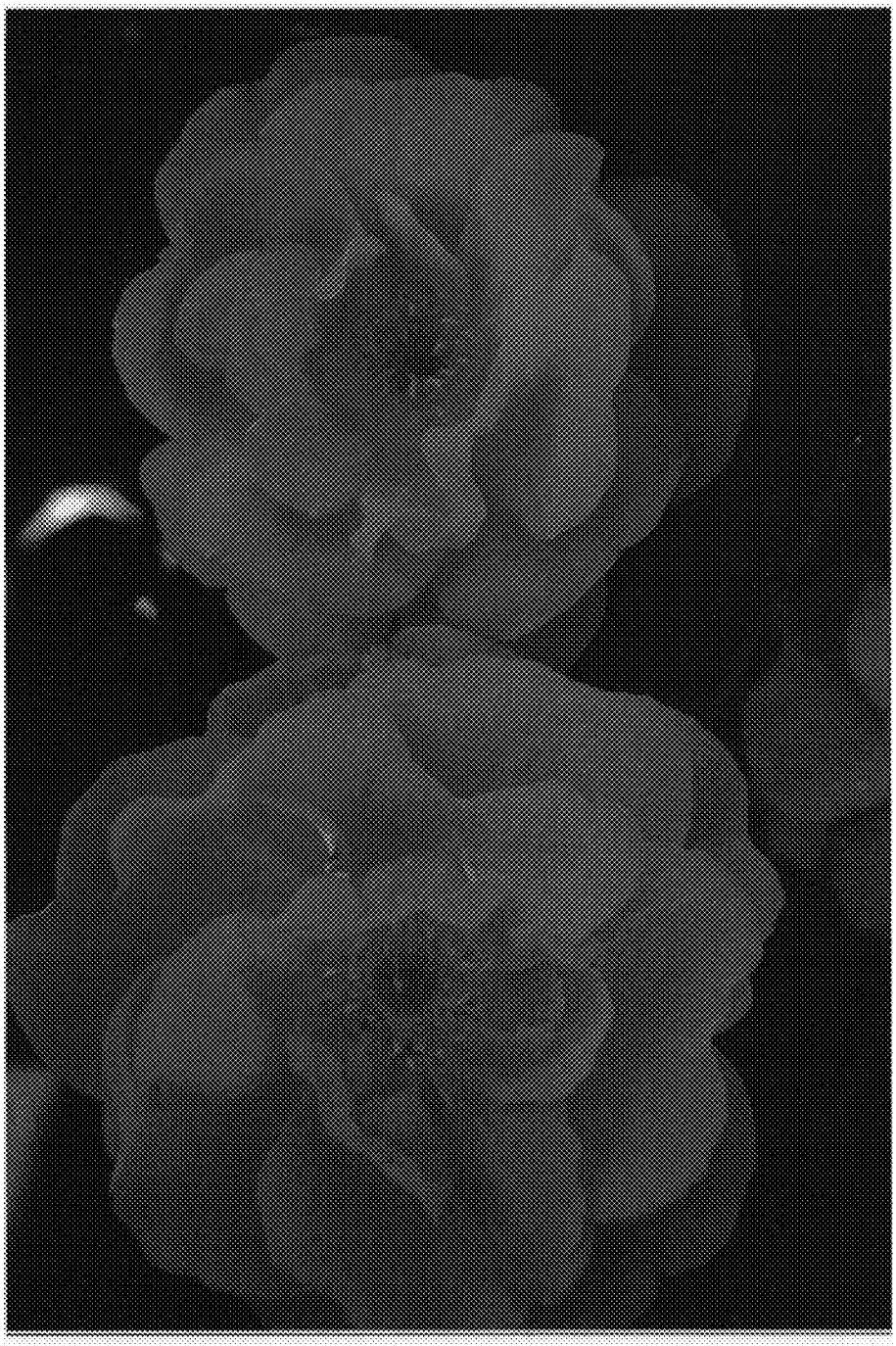

* * * * *